(12) United States Patent
Loescher et al.

(10) Patent No.: US 12,187,670 B2
(45) Date of Patent: Jan. 7, 2025

(54) METAL ORGANIC INTERACTIONS AT HYDROTHERMAL CONDITIONS

(71) Applicants: Grant Loescher, Tempe, AZ (US);
Everett Shock, Scottsdale, AZ (US);
Ian Gould, Phoenix, AZ (US); Hilairy Hartnett, Phoenix, AZ (US); Lynda B. Williams, Tempe, AZ (US)

(72) Inventors: Grant Loescher, Tempe, AZ (US);
Everett Shock, Scottsdale, AZ (US);
Ian Gould, Phoenix, AZ (US); Hilairy Hartnett, Phoenix, AZ (US); Lynda B. Williams, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 15 days.

(21) Appl. No.: 17/157,173

(22) Filed: Jan. 25, 2021

(65) Prior Publication Data
US 2021/0230088 A1    Jul. 29, 2021

Related U.S. Application Data

(60) Provisional application No. 62/965,513, filed on Jan. 24, 2020.

(51) Int. Cl.
| | |
|---|---|
| *C07C 37/60* | (2006.01) |
| *C07C 37/02* | (2006.01) |
| *C07C 45/29* | (2006.01) |
| *C07C 51/305* | (2006.01) |

(52) U.S. Cl.
CPC ........... *C07C 37/60* (2013.01); *C07C 37/02* (2013.01); *C07C 45/29* (2013.01); *C07C 51/305* (2013.01)

(58) Field of Classification Search
CPC ............................... C07C 17/12; C07C 25/06
USPC ........................................................ 562/418
See application file for complete search history.

(56) References Cited

U.S. PATENT DOCUMENTS 2,760,991 A * 8/1956 Toland
3,033,904 A * 5/1962 Braunwarth ............ C07C 37/58
568/747

OTHER PUBLICATIONS

Liu et al. Plasma Chem Plasma Process (2007) 27:496-503.*
Bosset et al Applied and Environmental Microbiology, Nov. 1986, p. 1117-1122.*
Abramowicz, D.A., 1995. Aerobic and anaerobic PCB biodegradation in the environment. Environmental Health Perspectives, 103(suppl 5), pp. 97-99.
Alonso, F., Beletskaya, I.P. and Yus, M., 2002. Metal-mediated reductive hydrodehalogenation of organic halides. Chemical Reviews, 102(11), pp. 4009-4092.
Aken, B.V., Correa, P.A. and Schnoor, J.L., 2010. Phytoremediation of polychlorinated biphenyls: new trends and promises. Environmental Science & Technology, 44(8), pp. 2767-2776.
Anderson Jr, H.R., Scheraga, H.A. and VanArtsdalen, E.R., 1953. Bromination of Hydrocarbons. VI. Photochemical and Thermal Bromination of Toluene. Bond Dissociation Energies. The Journal of Chemical Physics, 21(7), pp. 1258-1267.
Balducci, L., Bianchi, D., Bortolo, R., D'Aloisio, R., Ricci, M., Tassinari, R. and Ungarelli, R., 2003. Direct oxidation of benzene to phenol with hydrogen peroxide over a modified titanium silicalite. Angewandte Chemie International Edition, 42(40), pp. 4937-4940.
Barnard, J.A. and Ibberson, V.J., 1965. The gaseous oxidation of toluene II—The analytical results. Combustion and Flame, 9(2), pp. 149-157.
Bell, J.L. and Palmer, D.A., 1994. Experimental studies of organic acid decomposition. In Organic Acids in Geological Processes (pp. 226-269). Springer, Berlin, Heidelberg.
Benoit, S.D., Gallagher, W.E., Chan, D.B., Fukumoto, J.L. and Crisostomo, F.Q., 1997. Technology Transfer Report: Production Base Catalyzed Decomposition Process Guam, Mariana Islands (No. NFESC-TR-2075-ENV). Naval Facilities Engineering Service Center Port Hueneme CA., 402 pages.
Birch, A.J., 1944. 117. Reduction by dissolving metals. Part I. Journal of the Chemical Society, pp. 430-436.
Birch, A.J., Hinde, A.L. and Radom, L., 1980. A theoretical approach to the Birch reduction. Structures and stabilities of the radical anions of substituted benzenes. Journal of the American Chemical Society, 102(10), pp. 3370-3376.
Bockisch, C., Lorance, E. D., Hartnett, H. E., Shock, E. L., & Gould, I. R. (2018). Kinetics and mechanisms of dehydration of secondary alcohols under hydrothermal conditions. ACS Earth and Space Chemistry, 2(8), 821-832.
Bockisch, C., Lorance, E. D., Shaver, G., Williams, L. B., Hartnett, H. E., Shock, E. L., & Gould, I. R. (2019). Selective hydrothermal reductions using geomimicry. Green Chemistry, 21(15), 4159-4168.
Boltz, M., de Mattos, M. C., Esteves, P. M., Pale, P., & Louis, B. (2012). Green route for the chlorination of nitrobenzene. Applied Catalysis A: General, 449, 1-8.
Brunelle, D.J., Mendiratta, A.K. and Singleton, D.A., 1985. Reaction/ removal of polychlorinated biphenyls from transformer oil: treatment of contaminated oil with poly(ethylene glycol)/potassium hydroxide. Environmental Science & Technology, 19(8), pp. 740-746.
Bunnett, J.F., Garbisch Jr, E.W. and Pruitt, K.M., 1957. The "element effect" as a criterion of mechanism in activated aromatic nucleophilic substitution reactions. Journal of the American Chemical Society, 79(2), pp. 385-391.
Chen, X., Zhang, J., Fu, X., Antonietti, M. and Wang, X., 2009. Fe-g-C3N4-catalyzed oxidation of benzene to phenol using hydrogen peroxide and visible light. Journal of the American Chemical Society, 131(33), pp. 11658-11659.

(Continued)

*Primary Examiner* — Ana Z Muresan
(74) *Attorney, Agent, or Firm* — Fish & Richardson P.C.

(57) ABSTRACT

Oxidizing a first aromatic compound in the presence of a metal salt to yield a second aromatic compound includes combining the first aromatic compound, the metal salt, and water to yield an aqueous mixture, and heating the aqueous mixture at a temperature exceeding 200° C. to yield a reaction product that includes the second aromatic compound.

11 Claims, 7 Drawing Sheets

(56) References Cited

OTHER PUBLICATIONS

Cornwall, H.R., 1956. A summary of ideas on the origin of native copper deposits. Economic Geology, 51(7), pp. 615-631.
Cruse, A.M. and Seewald, J.S., 2006. Geochemistry of low-molecular weight hydrocarbons in hydrothermal fluids from Middle Valley, northern Juan de Fuca Ridge. Geochimica et Cosmochimica Acta, 70(8), pp. 2073-2092.
Cruse, A.M. and Seewald, J.S., 2010. Low-molecular weight hydrocarbons in vent fluids from the Main Endeavour Field, northern Juan de Fuca Ridge. Geochimica et Cosmochimica Acta, 74(21), pp. 6126-6140.
Cullis, C.F. and Ladbury, J.W., 1955. Kinetic studies of the oxidation of aromatic compounds by potassium permanganate. Part I. Toluene. Journal of the Chemical Society (Resumed), pp. 555-560.
Das, R. and Blanc, P.D., 1993. Chlorine gas exposure and the lung: a review. Toxicology and industrial health, 9(3), pp. 439-455.
Dombrowski, N., Teske, A. P., & Baker, B. J. (2018). Expansive microbial metabolic versatility and biodiversity in dynamic Guaymas Basin hydrothermal sediments. Nature Communications, 9(1), 1-13.
Doner, H.E. and Mortland, M.M., 1969. Benzene complexes with copper (II) montmorillonite. Science, 166(3911), pp. 1406-1407.
Dick, J.M., 2019. CHNOSZ: Thermodynamic calculations and diagrams for geochemistry. Frontiers in Earth Science, 7, 180, 18 pages.
Diot, H.R. and Young, D.T., 1991. Fluidized bed PCB incineration in Alaska. Remediation Journal, 1(2), pp. 199-209.
Elderfield, H. and Schultz, A., 1996. Mid-ocean ridge hydrothermal fluxes and the chemical composition of the ocean. Annual Review of Earth and Planetary Sciences, 24(1), pp. 191-224.
Falkowski, P., Scholes, R.J., Boyle, E.E.A., Canadell, J., Canfield, D., Elser, J., Gruber, N., Hibbard, K., Högberg, P., Linder, S. and Mackenzie, F.T., (2000). The global carbon cycle: a test of our knowledge of earth as a system. Science, 290(5490), pp. 291-296.
Fecteau, K. M., Gould, I. R., Glein, C. R., Williams, L. B., Hartnett, H. E., & Shock, E. L. (2019). Production of carboxylic acids from aldehydes under hydrothermal conditions: a kinetics study of benzaldehyde. ACS Earth and Space Chemistry, 3(2), 170-191.
Fu, X., Jamison, M., Jubb, A.M., Liao, Y., Aspin, A., Hayes, K., Glein, C.R. and Yang, Z., 2020. Effect of copper salts on hydrothermal oxidative decarboxylation: a study of phenylacetic acid. Chemical Communications, 56:2791-2794.
Glein, C. R., Gould, I. R., Lorance, E. D., Hartnett, H. E., & Shock, E. L. (2020). Mechanisms of decarboxylation of phenylacetic acids and their sodium salts in water at high temperature and pressure. Geochimica et Cosmochimica Acta, 269, 597-621.
Gomes, H.I., Dias-Ferreira, C. and Ribeiro, A.B., 2013. Overview of in situ and ex situ remediation technologies for PCB-contaminated soils and sediments and obstacles for full-scale application. Science of the Total Environment, 445, pp. 237-260.
Guo, C.C., Liu, Q., Wang, X.T. and Hu, H.Y., 2005. Selective liquid phase oxidation of toluene with air. Applied Catalysis A: General, 282(1-2), pp. 55-59.
Hansch, C., Leo, A. and Taft, R.W., 1991. A survey of Hammett substituent constants and resonance and field parameters. Chemical reviews, 91(2), pp. 165-195.
Helgeson, H.C., Kirkham, D.H. and Flowers, G.C., 1981. Theoretical prediction of the thermodynamic behavior of aqueous electrolytes at high pressures and temperatures; IV, Calculation of activity coefficients, osmotic coefficients, and apparent molal and standard and relative partial molal properties to 600 degrees C and 5kb. American Journal of Science, 281(10), 1249-1516.
Helgeson, H.C., Knox, A.M., Owens, C.E. and Shock, E.L., 1993. Petroleum, oil field waters, and authigenic mineral assemblages: Are they in metastable equilibrium in hydrocarbon reservoirs? Geochimica et Cosmochimica Acta, 57(14), pp. 3295-3339.
Ho, E.S. and Mauk, J.L., 1996. Relationship between organic matter and copper mineralization in the Proterozoic Nonesuch Formation, northern Michigan. Ore Geology Reviews, 11(1-3), pp. 71-87.

Houghton, R. A. (2007). Balancing the global carbon budget. Annual Reviews in Earth and Planetary Science, 35, 313-347.
Hutzinger, O., Choudhry, G.G., Chittim, B.G. and Johnston, L.E., 1985. Formation of polychlorinated dibenzofurans and dioxins during combustion, electrical equipment fires and PCB incineration. Environmental Health Perspectives, 60, pp. 3-9.
Jakobsson, S. and Holloway, J.R., 1986. Crystal—Liquid experiments in the presence of a C—O—H fluid buffered by graphite+ iron+ wustite: experimental method and near-liquidus relations in basanite. Journal of Volcanology and Geothermal Research, 29(1-4), pp. 265-291.
Kawka, O.E. and Simoneit, B.R., 1990. Polycyclic aromatic hydrocarbons in hydrothermal petroleums from the Guaymas Basin spreading center. Applied Geochemistry, 5(1-2), pp. 17-27.
Kesavan, L., Tiruvalam, R., Ab Rahim, M.H., bin Saiman, M.I., Enache, D.I., Jenkins, R.L., Dimitratos, N., Lopez-Sanchez, J.A., Taylor, S.H., Knight, D.W. and Kiely, C.J., 2011. Solvent-free oxidation of primary carbon-hydrogen bonds in toluene using Au—Pd alloy nanoparticles. Science, 331(6014), pp. 195-199.
Konn, C., Charlou, J.L., Donval, J.P., Holm, N.G., Dehairs, F. and Bouillon, S., 2009. Hydrocarbons and oxidized organic compounds in hydrothermal fluids from Rainbow and Lost City ultramafic-hosted vents. Chemical Geology, 258(3-4), pp. 299-314.
Kovacic, P. and Brace, N.O., 1954. Chlorination of aromatic compounds with metal chlorides. Journal of the American Chemical Society, 76(21), pp. 5491-5494.
Kubátová, A., Herman, J., Steckler, T.S., de Veij, M., Miller, D.J., Klunder, E.B., Wai, C.M. and Hawthorne, S.B., 2003. Subcritical (hot/liquid) water dechlorination of PCBs (Aroclor 1254) with metal additives and in waste paint. Environmental Science & Technology, 37(24), pp. 5757-5762.
Kuznetsova, N.I., Kuznetsova, L.I., Likholobov, V.A. and Pez, G.P., 2005. Hydroxylation of benzene with oxygen and hydrogen over catalysts containing Group VIII metals and heteropoly compounds. Catalysis Today, 99(1-2), pp. 193-198.
Mabey, W. and Mill, T., 1978. Critical review of hydrolysis of organic compounds in water under environmental conditions. Journal of Physical and Chemical Reference Data, 7(2), pp. 383-415.
McCollom, T.M., Seewald, J.S. and Simoneit, B.R.T., 2001. Reactivity of monocyclic aromatic compounds under hydrothermal conditions. Geochimica et Cosmochimica Acta, 65(3), pp. 455-468.
McCollom, T. M. (2013). The influence of minerals on decomposition of the n-alkyl-α-amino acid norvaline under hydrothermal conditions. Geochimica et Cosmochimica Acta, 104, 330-357.
McMillan, W.J. and Panteleyev, A., 1980. Ore Deposit Models—1. Porphyry Copper Deposits. Geoscience Canada, 7(2):52-63.
Molinari, R. and Poerio, T., 2010. Remarks on studies for direct production of phenol in conventional and membrane reactors. Asia-Pacific Journal of Chemical Engineering, 5(1), pp. 191-206.
Mortland, M.M. and Pinnavaia, T.J., 1971. Formation of copper (II) arene complexes on the interlamellar surfaces of montmorillonite. Nature Physical Science, 229(3):75-77.
Moen, A. and Nicholson, D.G., 1995. Reduction of copper(II) with subsequent disproportionation of copper(I) during the hydrothermal syntheses of microporous silicoaluminium phosphates sapo-5 and -11. Journal of the Chemical Society, Faraday Transactions, 91(19), pp. 3529-3535.
Necsoiu, I., Balaban, A. T., Pascaru, I., Sliam, E., Elian, M., & Nenitzescu, C. D. 1963. The mechanism of the etard reaction. Tetrahedron, 19(7), 1133-1142.
Olah, G.A., 1971. Aromatic substitution. XXVIII. Mechanism of electrophilic aromatic substitutions. Accounts of Chemical Research, 4(7), pp. 240-248.
Owen, B. B., Miller, R. C., Milner, C. E., & Cogan, H. L. (1961). The dielectric constant of water as a function of temperature and pressure. The Journal of Physical Chemistry, 65(11), 2065-2070.
Paine, A.J., 1987. Mechanisms and models for copper mediated nucleophilic aromatic substitution. 2. Single catalytic species from three different oxidation states of copper in an Ullmann synthesis of triarylamines. Journal of the American Chemical Society, 109(5), pp. 1496-1502.

(56) References Cited

OTHER PUBLICATIONS

Philippi, G. T. (1965). On the depth, time and mechanism of petroleum generation. Geochimica et Cosmochimica Acta, 29(9), 1021-1049.

Peng, J., Shi, F., Gu, Y., & Deng, Y. (2003). Highly selective and green aqueous-ionic liquid biphasic hydroxylation of benzene to phenol with hydrogen peroxide. Green Chemistry, 5(2), 224-226.

Persson, I., Penner-Hahn, J.E. and Hodgson, K.O., 1993. An EXAFS spectroscopic study of solvates of copper(I) and copper(II) in acetonitrile, dimethyl sulfoxide, pyridine, and tetrahydrothiophene solutions and a large-angle X-ray scattering study of the copper(II) acetonitrile solvate in solution. Inorganic Chemistry, 32(11), pp. 2497-2501.

ACS.org [online], "What's New in Phenol Production?" available on or before Apr. 10, 2016, via Internet Archive: Wayback Machine URL <http://web.archive.org/web/20160410162703/https://www.acs.org/content/acs/en/pressroom/cutting-edge-chemistry/what-s-new-in-phenol-production-.html>, retrieved on Apr. 27, 2022, URL <https://www.acs.org/content/acs/en/pressroom/cutting-edge-chemistry/what-s-new-in-phenol-production-.html>, 3 pages.

Pinnavaia, T.J. and Mortland, M.M., 1971. Interlamellar metal complexes on layer silicates. I. Copper(II)-arene complexes on montmorillonite. The Journal of Physical Chemistry, 75(26), pp. 3957-3962.

Powell, K.J., Brown, P.L., Byrne, R.H., Gajda, T., Hefter, G., Leuz, A.K., Sjöberg, S. and Wanner, H., 2007. Chemical Speciation of Environmentally Significant Metals with Inorganic Ligands Part 2: The Cu2+-OH- , Cl- , CO32- , SO42- , and PO43-systems. Pure Appl. Chem., vol. 79, No. 5, 895-950.

Rahuman, M.S.M.M., Pistone, L., Trifirò, F. and Miertus, S., Nov. 2000. Destruction technologies for polychlorinated biphenyls (PCBs). In Proceedings of Expert Group Meetings on POPs and Pesticides Contamination (vol. 16, No. 6, pp. 405-423).

Raymont, J.E.G. and Shields, J., 1963. Toxicity of copper and chromium in the marine environment. Int. J. Air Water Pollut, 7, pp. 435-443.

Robinson, K. J., Gould, I. R., Fecteau, K. M., Hartnett, H. E., Williams, L. B., & Shock, E. L. (2019). Deamination reaction mechanisms of protonated amines under hydrothermal conditions. Geochimica et Cosmochimica Acta, 244, 113-128.

Reichle, W.T., 1970. The nature of the hydrolysis of chlorobenzene over calcium phosphate apatite. Journal of Catalysis, 17(3), pp. 297-305.

Rupert, J.P., 1973. Electron spin resonance spectra of interlamellar copper (II)-arene complexes on montmorillonite. The Journal of Physical Chemistry, 77(6), pp. 784-790.

Sambiagio, C., Marsden, S.P., Blacker, A.J. and McGowan, P.C., 2014. Copper catalysed Ullmann type chemistry: from mechanistic aspects to modern development. Chemical Society Reviews, 43(10), pp. 3525-3550.

Seewald, J.S., 2001. Aqueous geochemistry of low molecular weight hydrocarbons at elevated temperatures and pressures: constraints from mineral buffered laboratory experiments. Geochimica et Cosmochimica Acta, 65(10), pp. 1641-1664.

Seewald, J.S., 1994. Evidence for metastable equilibrium between hydrocarbons under hydrothermal conditions. Nature, 370(6487), 285-287.

Seewald, J.S., Zolotov, M.Y. and McCollom, T., 2006. Experimental investigation of single carbon compounds under hydrothermal conditions. Geochimica et Cosmochimica Acta, 70(2), 446-460.

Seewald, J. S. (1996). Mineral redox buffers and the stability of organic compounds under hydrothermal conditions. MRS Online Proceedings Library Archive, 432:317-331.

Seewald, J.S., 1994. Evidence for metastable equilibrium between hydrocarbons under hydrothermal conditions. Nature, 370(6487), pp. 285-287.

Shipp, J., Gould, I. R., Herckes, P., Shock, E. L., Williams, L. B., & Hartnett, H. E. (2013). Organic functional group transformations in water at elevated temperature and pressure: Reversibility, reactivity, and mechanisms. Geochimica et Cosmochimica Acta, 104, 194-209.

Shipp, J. A., Gould, I. R., Shock, E. L., Williams, L. B., & Hartnett, H. E. (2014). Sphalerite is a geochemical catalyst for carbon-hydrogen bond activation. Proceedings of the National Academy of Sciences, 111(32), 11642-11645.

Shock, E.L., 1994. Application of thermodynamic calculations to geochemical processes involving organic acids. In Organic acids in geological processes (pp. 270-318). Springer, Berlin, Heidelberg.

Shock, E.L., Sassani, D.C., Willis, M. and Sverjensky, D.A., 1997. Inorganic species in geologic fluids: correlations among standard molal thermodynamic properties of aqueous ions and hydroxide complexes. Geochimica et Cosmochimica Acta, 61(5), pp. 907-950.

Shock, E.L., 2009. Minerals as energy sources for microorganisms. Economic Geology, 104(8), pp. 1235-1248.

Sokolov, O., Hurley, M.D., Wallington, T.J., Kaiser, E.W., Platz, J., Nielsen, O.J., Berho, F., Rayez, M.T. and Lesclaux, R., 1998. Kinetics and mechanism of the gas-phase reaction of C1 atoms with benzene. The Journal of Physical Chemistry A, 102(52), pp. 10671-10681.

Silva, G.C., Carvalho, N.M., Horn Jr, A., Lachter, E.R. and Antunes, O.A., 2017. Oxidation of aromatic compounds by hydrogen peroxide catalyzed by mononuclear iron (III) complexes. Journal of Molecular Catalysis A: Chemical, 426, pp. 564-571.

Simoneit, B. R., & Lonsdale, P. F. (1982). Hydrothermal petroleum in mineralized mounds at the seabed of Guaymas Basin. Nature, 295(5846), 198-202.

Smith, R.M. and Martell, A.E., 1976. Critical stability constants: inorganic complexes (vol. 4, pp. 96-103). New York: Plenum Press.

St Clair, B., Pottenger, J., Debes, R., Hanselmann, K. and Shock, E., 2019. Distinguishing biotic and abiotic iron oxidation at low temperatures. ACS Earth and Space Chemistry, 3(6), 905-921.

Sudharshan, S., Naidu, R., Mallavarapu, M. and Bolan, N., 2012. DDT remediation in contaminated soils: a review of recent studies. Biodegradation, 23(6), pp. 851-863.

Sverjensky, D.A., Shock, E.L. and Helgeson, H.C., 1997. Prediction of the thermodynamic properties of aqueous metal complexes to 1000° C. and 5 kb. Geochimica et Cosmochimica Acta, 61(7), 1359-1412.

Tanemura, K., Suzuki, T., Nishida, Y., Satsumabayashi, K. and Horaguchi, T., 2003. Halogenation of aromatic compounds by N-chloro- , N-bromo- , and N-iodosuccinimide. Chemistry Letters, 32(10), pp. 932-933.

Tassi, F., Capecchiacci, F., Cabassi, J., Calabrese, S., Vaselli, O., Rouwet, D., Pecoraino, G. and Chiodini, G., 2012. Geogenic and atmospheric sources for volatile organic compounds in fumarolic emissions from Mt. Etna and Vulcano Island (Sicily, Italy). Journal of Geophysical Research: Atmospheres, 117(D17), 21 pages.

Van, K.V. and Habashi, F., 1972. Identification and thermal stability of copper (I) sulfate. Canadian Journal of Chemistry, 50(23), pp. 3872-3875.

Vaselli, O., Tassi, F., Montegrossi, G., Capaccioni, B. and Giannini, L., 2006. Sampling and analysis of volcanic gases. Acta Vulcanologica, 18(1-2), p. 65-76.

Venturi, S., Tassi, F., Gould, I. R., Shock, E. L., Hartnett, H. E., Lorance, E. D., & Vaselli, O. (2017). Mineral-assisted production of benzene under hydrothermal conditions: Insights from experimental studies on C6 cyclic hydrocarbons. Journal of Volcanology and Geothermal Research, 346, 21-27.

Wang, S., 2005. Copper leaching from chalcopyrite concentrates. JOM, 57(7), pp. 48-51.

Wang, C.Y., Zhou, M.F., Qi, L., Hou, S., Gao, H., Zhang, Z. and Malpas, J., 2006. The Zhaotong native copper deposit associated with the Permian Emeishan flood basalts, Yunnan, Southwest China. International Geology Review, 48(8), pp. 742-753.

Wiley, J.R., Chen, E.C.M., Chen, E.S.D., Richardson, P., Reed, W.R. and Wentworth, W.E., 1991. The determination of absolute electron affinities of chlorobenzenes, chloronaphthalenes and chlorinated biphenyls from reduction potentials. Journal of Electroanalytical Chemistry and Interfacial Electrochemistry, 307(1-2), pp. 169-182.

(56) References Cited

OTHER PUBLICATIONS

Winder, C., 2001. The toxicology of chlorine. Environmental research, 85(2), pp. 105-114.

Withers, R.M.J. and Lees, F.P., 1985. The assessment of major hazards: The lethal toxicity of chlorine: Part 1, Review of information on toxicity. Journal of hazardous materials, 12(3), pp. 231-282.

Yang, J.H., Sun, G., Gao, Y., Zhao, H., Tang, P., Tan, J., Lu, A.H. and Ma, D., 2013. Direct catalytic oxidation of benzene to phenol over metal-free graphene-based catalyst. Energy & Environmental Science, 6(3), pp. 793-798.

Yang, Z., Gould, I. R., Williams, L. B., Hartnett, H. E., & Shock, E. L. (2012). The central role of ketones in reversible and irreversible hydrothermal organic functional group transformations. Geochimica et Cosmochimica Acta, 98, 48-65.

Zhang, C., Tang, C. and Jiao, N., 2012. Recent advances in copper-catalyzed dehydrogenative functionalization via a single electron transfer (SET) process. Chemical Society Reviews, 41(9), pp. 3464-3484.

* cited by examiner

METAL ORGANIC INTERACTIONS AT HYDROTHERMAL CONDITIONS

CROSS-REFERENCE TO RELATED APPLICATION

This application claims the benefit of U.S. Patent Application No. 62/965,513 entitled "SYNTHESIS OF PHENOL AND COPPER METAL" and filed on Jan. 24, 2020, which is incorporated herein by reference in its entirety.

TECHNICAL FIELD

This invention relates to a synthetic process including oxidation of benzene with copper sulfate to yield phenol and copper metal.

BACKGROUND

Over 10 million metric tons of phenol are produced annually, making it a commodity chemical with a multibillion-dollar market. Phenol is primarily used as an intermediate in the production of polymers and adhesives. The current industrial production method is a complex, multi-step process that limits yield and produces unwanted side products. Typical synthesis routes use non-metal oxidants (e.g., oxygen or hydrogen peroxide) and proceed through an alkylated intermediate with more than 6 carbons.

SUMMARY

This disclosure describes reaction pathways for organic reactions at hydrothermal conditions. Various reactions include benzene oxidation with copper, toluene oxidation with copper, and dehalogenation of aromatic compounds with copper. The reactions are one-pot syntheses of industrially significant compounds using relatively benign, Earth-abundant materials. These hydrothermal oxidations serve as a geomimetic alternative for the current industrial methods. In addition to the reaction pathways, this disclosure demonstrates metal speciation in oxidation reactions. Metal speciation can lead to different organic and inorganic products, such that the reaction can be tuned to produce desired products by adjusting the solution composition and the metal speciation.

In a first general aspect, oxidizing a first aromatic compound in the presence of a metal salt to yield a second aromatic compound includes combining the first aromatic compound, the metal salt, and water to yield an aqueous mixture, and heating the aqueous mixture at a temperature exceeding 200° C. to yield a reaction product comprising the second aromatic compound.

Implementations of the first general aspect may include one or more of the following features.

In some implementations, the first aromatic compound is benzene. In some implementations, the metal is copper(II). In one example, the first aromatic compound is benzene, the metal salt is copper sulfate, and the second aromatic compound is phenol. A selectivity of this reaction can exceed 96%. A yield of this reaction can exceed 40%. The reaction product can include copper metal.

In some implementations, the first aromatic compound is benzene. In some implementations, the metal is copper(II). In one example, the first aromatic compound is benzene, the metal salt is copper chloride, and the second aromatic compound is chlorobenzene.

In some implementations, oxidizing the first aromatic compound to yield the second aromatic compound occurs in a single vessel.

In some implementations, the metal comprises iron. The metal salt can be iron(III) chloride.

In some implementations, the first aromatic compound is toluene. In some implementations, the metal is copper(II). The metal salt can be copper(II) chloride. The second aromatic compound can be benzyl alcohol. The benzyl alcohol can be further oxidized with copper(II) to yield benzaldehyde. The benzaldehyde can be further oxidized with copper(II) to yield benzoic acid. The reaction product can include benzyl toluene.

In a second general aspect, reducing a first aromatic compound in the presence of a metal to yield a second aromatic compound includes combining the first aromatic compound, the metal, and water to yield an aqueous mixture, and heating the aqueous mixture at a temperature exceeding 200° C. to yield a reaction product comprising the second aromatic compound.

Implementations of the second general aspect may include one or more of the following features.

In some implementations, the first aromatic compound is halogenated. In some implementations, the second aromatic compound is dehalogenated. In one example, the first aromatic compound is chlorobenzene and the second aromatic compound comprises benzene, phenol, or both.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

Figure 2:
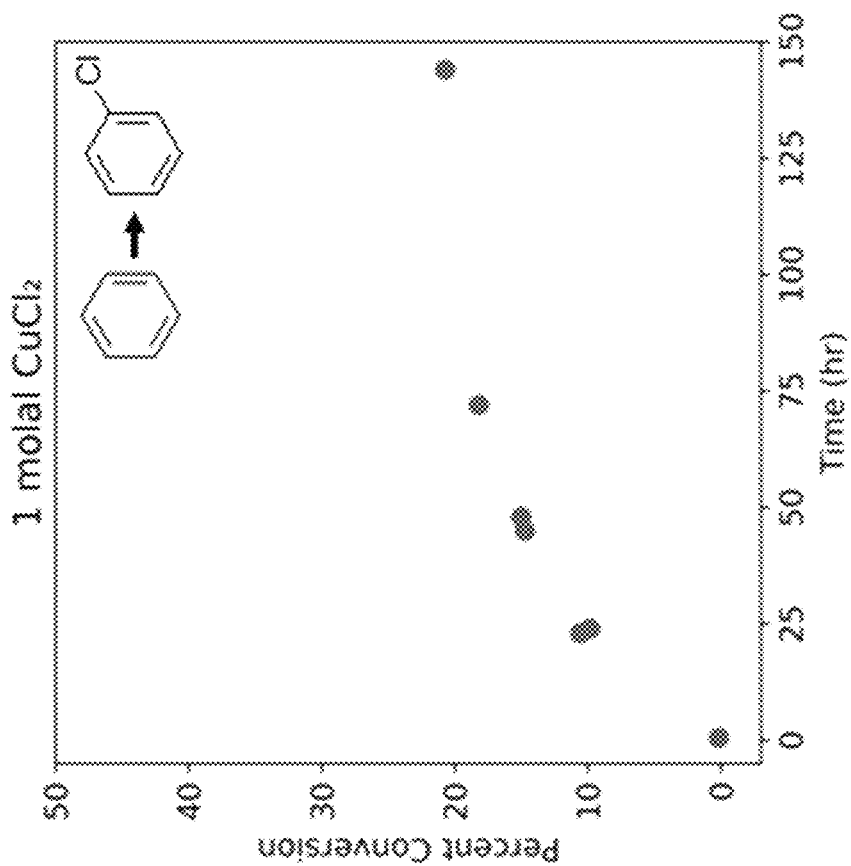
FIG. 2 shows percent conversion as a function of time for the conversion of benzene to chlorobenzene using $CuCl_2$.

This disclosure describes reaction pathways for organic reactions with metals in an aqueous solvent at hydrothermal conditions. As used herein, "hydrothermal conditions" generally include temperatures exceeding 200° C. (e.g., up to 300° C., 400° C., or 500° C.) and pressures exceeding that of the liquid vapor saturation curve. Reactant concentrations typically exceed 0.01 molal (m); the concentration of each reactant can be selected to yield desired results. Reaction times can vary between 15 minutes and 2 weeks. Although examples include benzene oxidation with copper, toluene oxidation with copper, and dehalogenation of aromatic compounds with copper, other metals and organic compounds can also be used. Examples of suitable metals include copper, iron, chromium, molybdenum, tungsten, vanadium, niobium, tantalum, titanium, zirconium, manganese, nickel, palladium, platinum, silver, gold, cobalt, rhodium, and iridium. Examples of suitable metal salts include metal sulfates, metal halides, metal phosphates, metal nitrates, metal nitrites, metal carbonates.

Oxidation of Benzene

Benzene can be oxidized with copper sulfate and copper chloride under hydrothermal conditions. The oxidation reactions described here represent unconventional pathways to the respective products, at least because the anion influences the reaction products. If Cu(II) were the reagent and Cl⁻ and $SO_4^{-2}$ were simply spectators, both salts would typically yield the same products and have similar kinetics. However, these reactions reveal two different substituents on the oxidized benzene and two different reduced inorganic products. When $CuSO_4$ is used as an oxidant, benzene is oxidized to phenol and the remaining inorganic material is metallic Cu. When $CuCl_2$ is the oxidant, benzene is oxidized to chlorobenzene and the inorganic precipitate appears to be CuCl(s). The inorganic products suggest that $CuCl_2$ favors a single electron transfer as implied by the conversion of Cu(II) into a Cu(I) species. The oxidation with $CuSO_4$ follows a different reaction mechanism. Since the Cu(II) is fully reduced to Cu(0), the oxidation may proceed though a single or double electron transfer. The proposed mechanisms for the observed reactions are guided by the speciation of Cu in solution and the behavior Cu(II) as an oxidant.

The mechanism for benzene oxidation with $CuSO_4$ under hydrothermal conditions is shown below. The first step is a single electron transfer from benzene to Cu(II). In the second step, after the radical cation is formed, a hydroxide ion or water molecule acts as a nucleophile and bonds to the positive charge. This forms a neutral radical compound which is oxidized by another Cu(II) in the third step, turning the radical cation into a carbocation. In the final step, the molecule deprotonates at the site of the hydroxide, and the electrons of the deprotonated C—H bond form a pi bond and restore aromaticity.

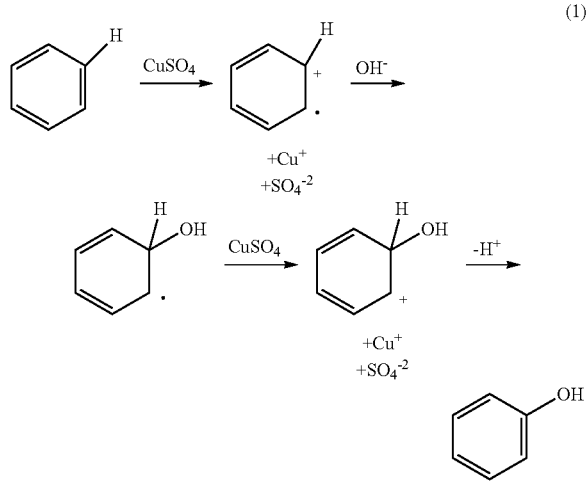

(1)

This mechanism leads to the formation of Cu(I) from two separate single-electron transfers. A disproportionation of Cu(I) is believed to result in metallic Cu. In aqueous solutions, disproportionation favors the Cu(II) and Cu(0) oxidation states over Cu(I), at least because of the increased ability for these species to interact with water molecules. There is more energy released in the hydration of Cu(II) than Cu(I), suggesting that it is energetically favorable for Cu to be in the +2 oxidation state. The disproportionation of copper is thought to be controlled at least in part by the properties of the solution it is dissolved in, suggesting that intermolecular forces between the solvent and the copper species can determine the equilibria between the redox states of copper species. Cu(I) and Cu(II) complexes are thought to influence the equilibrium of the disproportionation reaction:

$$2Cu^+ \rightleftharpoons Cu + Cu^{+2} \qquad (2)$$

Complexes influence the activity of free ions and could shift the equilibrium of the disproportionation reaction. The formation of Cu(I) complexes consumes $Cu^+$ ions, shifting the equation to the left to favor reactants. The formation of Cu(II) complexes consumes $Cu^{+2}$ ions, shifting the reaction to the right to favor products.

The mechanism for chlorinating benzene with $CuCl_2$ under hydrothermal conditions, shown below, proceeds similarly to the oxidation of benzene to phenol. The initial step is a single-electron transfer from a pi bond of the benzene ring to yield Cu (I) and a benzene radical cation. In the second step, the cation is attacked by a chloride ion from solution or by an adjacent copper chloride complex leaving a neutral radical compound. In the third step, the radical undergoes another single-electron transfer leaving a cation. Finally, the molecule deprotonates at the position of the chloride bond. The electrons from the broken C—H bond restore aromaticity to the system by forming a π-bond. The resulting product is chlorobenzene—no phenol is present. The inorganic precipitate is CuCl(s), and no metallic Cu is observed. Thus, the copper products are believed to be reduced by one electron rather than two.

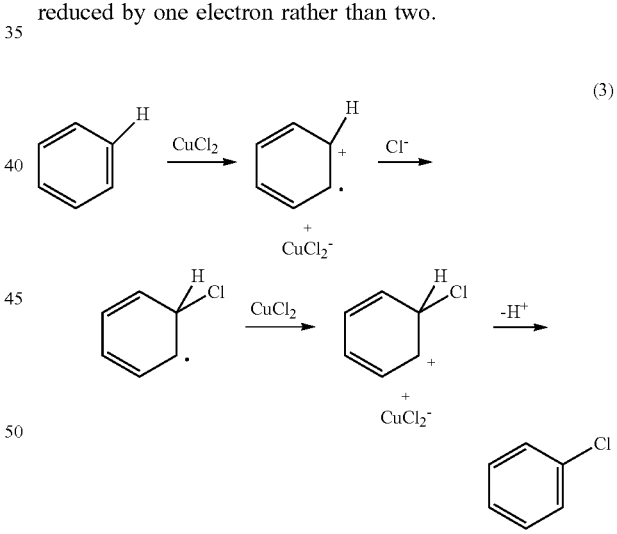

(3)

Oxidation of Toluene

A reaction scheme for the oxidation of toluene by Cu(II) under hydrothermal conditions is shown below. This scheme includes the complexation of toluene with two Cu(II) species that do not disrupt the aromaticity of toluene but rather act as electron withdrawing groups. The methyl group then deprotonates and transfers the σ electrons of the C—H bond into the π aromatic system to form a benzyl cation. The cation then reacts with a hydroxide molecule to form benzyl alcohol. Once produced, benzyl alcohol can be further oxidized to benzaldehyde and benzoic acid. After benzaldehyde is produced, it can be hydrolyzed, oxidized by Cu(II), and deprotonated to yield benzoic acid.

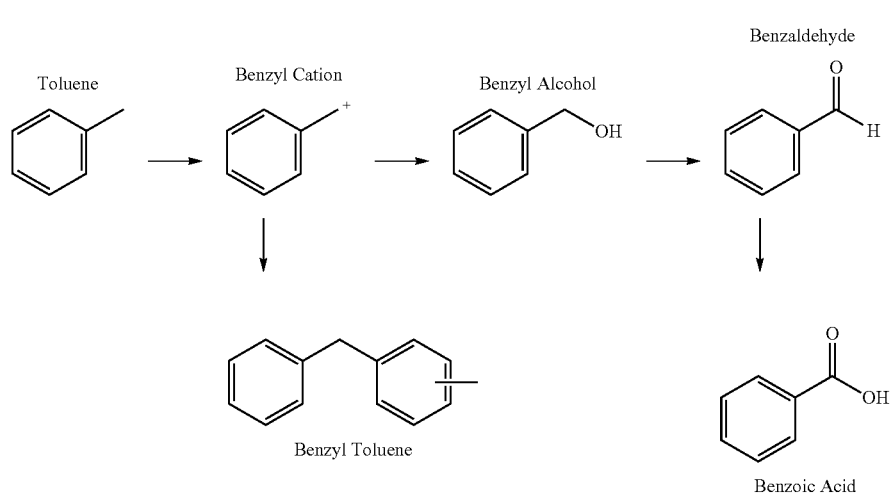

(4)

The balanced reactions for this scheme are shown below. Cu(II) and Cu(I) exist as a variety of chloride complexes. In reaction 5, toluene is oxidized by Cu(II) to form a benzyl cation. The benzyl cation reacts with a hydroxide ion to yield benzyl alcohol in reaction 6. Benzyl alcohol is then oxidized by Cu(II) through a series of single electron transfers to yield benzaldehyde and two protons in reaction 7. In reaction 8, benzaldehyde is oxidized by Cu(II) via two single electron transfers and hydrated with a water molecule to form benzoic acid and two protons. The benzyl cation also undergoes electrophilic aromatic substitution in reaction 9, with toluene acting as a nucleophile.

$$C_6H_5CH_3 + 2Cu(II) = C_6H_5CH_2^+ + 2Cu(I) + H^+ \quad (5)$$

$$C_6H_5CH_2^+ + OH^- = C_6H_5CH_2OH \quad (6)$$

$$C_6H_5CH_2OH + 2Cu(II) = C_6H_5CHO + 2Cu(I) + 2H^+ \quad (7)$$

$$C_6H_5CHO + 2Cu(II) + H_2O = C_6H_5COOH + 2Cu(I) + 2H^+ \quad (8)$$

$$C_6H_5CH_2^+ + C_6H_5CH_3 = C_6H_5CH_2C_6H_5CH_3 \quad (9)$$

Aromatic Dehalogenation

There are two predominant products when chlorobenzene is subject to hydrothermal conditions in the presence of copper. One main product is phenol, which is the result of a substitution. There is no oxidation or reduction in the substitution pathway, and copper is not consumed in the reaction. The reaction is summarized for chlorobenzene:

$$C_6H_5Cl + H_2O = C_6H_5OH + H^+ + Cl^- \quad (10)$$

Another main product is benzene. The presence of benzene is believed to be the result of chlorobenzene reduction, meaning that copper is acting as a reductant. This reaction is:

$$C_6H_5Cl + Cu + H^+ = C_6H_6 + Cu^+ \quad (11)$$

To produce the hydrocarbons observed in these reactions, chlorobenzene is reduced by copper. The proposed reduction mechanism is carried out through a series of single-electron transfers shown below.

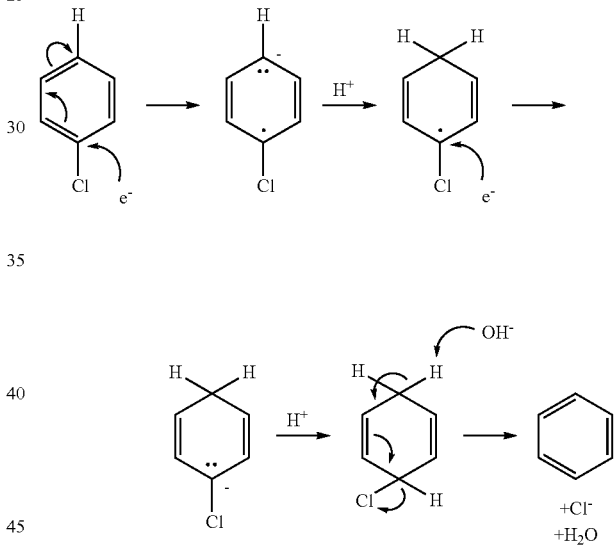

(12)

This mechanism can be generalized to other aryl halides. The reaction begins with a single electron transfer from the copper metal to the aromatic system. This extra electron causes the aromatic system to be disrupted and a pair of electrons shifts to a single carbon producing a radical anion. The radical anion bonds with a proton in solution, leaving a diene radical. The molecule gains another single electron from the copper and becomes an anion with a lone pair of electrons. At this point, the anion bonds with another proton and forms a halogenated cyclohexadiene. The chloride acts as a leaving group and the compound becomes a diene cation. The diene cation deprotonates, and electrons that formerly made up the C—H bond are transferred into the pi bond system to restore aromaticity. This results in the dehalogenation of the original compound, effectively replacing the halogen with a hydrogen.

The path from chlorobenzene to phenol, shown below, is a substitution reaction in which a halogen group is replaced by a hydroxyl group, with water acting as a nucleophile.

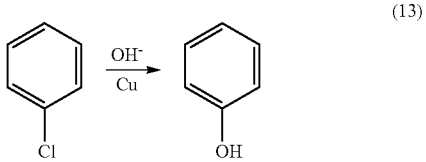
(13)

Chlorotoluene and chloronaphthalene can also be dehalogenated in the presence of copper. The chlorinated aromatic compound reacts to form the alcohol that results from a substitution of the halogen group with a hydroxyl group. The corresponding reactions are given by:

$$C_6H_4CH_3Cl+H_2O \rightleftharpoons C_6H_4CH_3OH+H^+ \quad (14)$$

$$C_{10}H_7Cl+H_2O \rightleftharpoons C_{10}H_7OH+H^+ \quad (15)$$

Additionally, these reactions produce hydrocarbons that result from the reductive substitution of the chlorine with hydrogen given by:

$$C_6H_4CH_3Cl+Cu+H^+ \rightleftharpoons C_6H_5CH_3+Cu^+ \quad (16)$$

$$C_{10}H_7Cl+Cu+H^+ \rightleftharpoons C_{10}H_8+Cu^+ \quad (17)$$

The overall conversion was found to be higher for chlorobenzene, lower for chloronaphthalene, and intermediate for chlorotoluene. The hydrocarbon to alcohol ratio also follows the trend napthyl>methyl>H. This suggests that the substituents also affect the reductive pathway.

EXAMPLES

Hydrothermal Reaction Vessels

Hydrothermal experiments were carried out in fused silica glass tubes supplied by Technical Glass Products. Tubing had an inner diameter of 2 mm and an outer diameter of 6 mm. The tubes were cut to 8-inch lengths and sealed to close one end. After sealing, the tubes were annealed overnight at 1140° C.

Reaction vessels were loaded with 300 µL of water measured by Hamilton gastight syringes. Deionized water with a resistance of 18.2 MΩ was obtained from a Barnstead Diamond Ultrapure water system. To remove oxygen from the experiments all water was sparged with ultra-high purity argon for at least one hour before being loaded into tubes. Organic reagents were added by volume using a 10 µL gastight Hamilton syringe. The organic concentration was varied to fit the needs of the experiment. Benzene oxidation experiments used 8 µL of benzene. Toluene oxidation experiments used 4 µL of toluene. Aromatic dehalogenation experiments used 8 µL of chlorobenzene in the experiments comparing effects of copper added, and 5 µL of respective organic in the experiments comparing the effects of different functional groups. All organic reagents were selected to be the highest possible purity. After the tubes were loaded with reagents and water, they were immediately frozen in liquid nitrogen to prevent the evaporation of the organic compound.

The inorganic reagents used in these experiments were CuCl$_2$, CuSO$_4$, and 23 µm grain size Cu powder. For benzene oxidation and aromatic dehalogenation experiments, the copper salt and the copper powder were measured by mass and added directly to the tube. High concentration salt solutions were not added directly to the tubes because of difficulty of freezing and sealing. Solutions with high salt concentrations tended to shatter the tubes as they thawed. In the lower concentration toluene oxidation experiments, a CuCl$_2$ solution was used in place of water. The copper solutions received the same treatment as the pure water experiments.

The tubes were submerged in liquid nitrogen so that the reactants were all frozen just below the surface of the liquid nitrogen. The tubes were then evacuated with a rough pump to <80 mTorr to remove air from the reaction vessel. While under vacuum the tubes were flame sealed using a hydrogen torch. The seal was made directly above the reagents to minimize headspace in the reaction vessels.

Reaction Conditions

The glass reaction vessels were placed in stainless steel tubes to contain the glass in the event of shattering. The reaction vessels were heated to the desired temperature in Gas Chromatography (GC) ovens. The temperature used in the experiments was 250° C. and the duration ranged from 0.5 to 144 hours. The temperature was monitored by the GC oven and monitored by a thermocouple. After the desired experimental duration, the tubes were taken out of the GC oven and quenched in room temperature water. Experiments were then analyzed or frozen for later analysis.

Sample Processing

Once cooled to ambient temperature, approximately 25° C., the reaction vessels were scored and broken with a pipe cutter near the middle of the tube so that approximately half of the liquid was in each half of the tube segments. The liquid was removed with a Pasteur pipet and transferred to a 4 mL silanized glass vial. All experiments were extracted by adding 3 mL dichloromethane (DCM) with dodecane as an internal standard. The vials were lightly shaken for at least 10 minutes to extract all of the organic material. Lastly, an aliquot of the DCM containing the sample was pipetted into a 1.5 mL Agilent trace clean amber autosampler vial.

Gas Chromatography Analysis

The products and reactants were quantified using a Bruker-Scion 456 gas chromatograph with an autosampler. The GC system used a Supelco Equity-5 column and a flame ionization detector. The autosampler was configured to inject 1 µL of sample. The injector temperature was 275° C. The flow rate of the helium carrier gas was 1 ml/min. The detector was set to 300° C. The temperature rates programed into the GC method are given in Table 1.

The mass balance of these experiments was determined by quantifying total molality of organic at the end of the experiments and comparing it to the starting concentration. The reagents are used in trace quantities and the presence of inorganic solids introduces a surface that organic reagents and products tend to stick to. This makes it difficult to fully extract the organic products to achieve complete mass balance.

TABLE 1

GC Temperature Program Parameters

| Rate (° C./min) | Temperature (° C.) | Time (min) | Total Time (min) |
|---|---|---|---|
| Initial | 40 | 0 | 0 |
| 10 | 140 | 0 | 10 |
| 5 | 220 | 0 | 26 |
| 20 | 300 | 15 | 45 |

Oxidation of Aromatic Compounds with Cu(II) Salts

Benzene was oxidized using both CuCl$_2$ and CuSO$_4$ to produce substituted aromatic molecules. In the CuCl$_2$ experiments, the product was chlorobenzene. In the CuSO$_4$ experiments, the product was phenol. The reduced form of copper produced in the experiments was also different depending on which copper salt was used. When $CuCl_2$ was used, the copper turns to a white, acid-soluble solid with the appearance of CuCl(s). In the experiments using $CuSO_4$, the precipitate appeared to be Cu(0) based on its color and metallic luster.

Reaction Time Series

Figure 1:
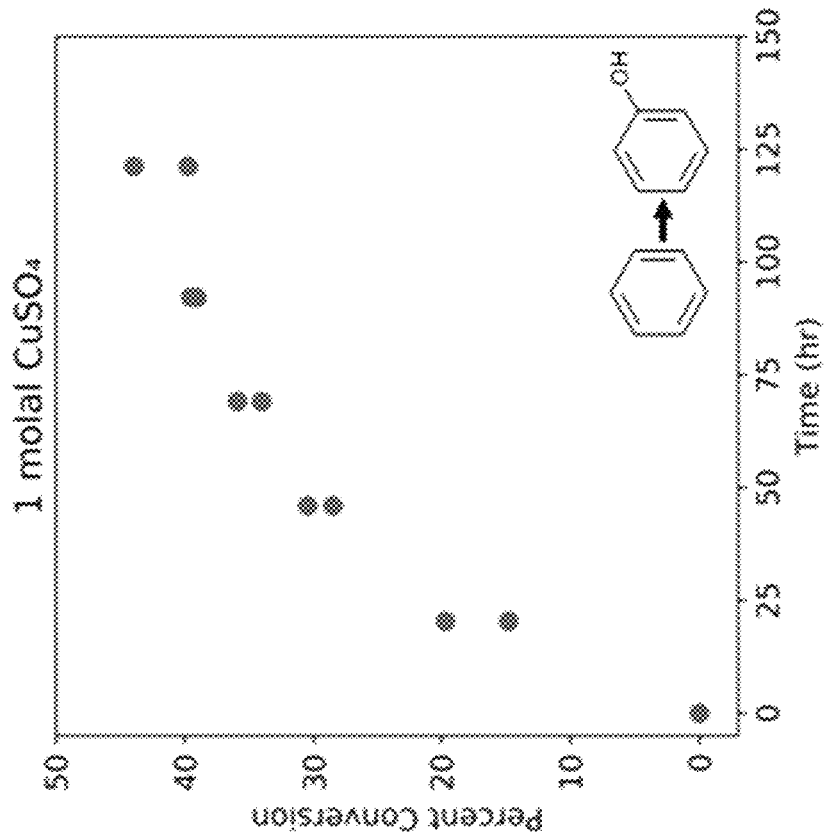
FIG. 1 shows percent conversion as a function of time for the conversion of benzene to phenol using $CuSO_4$.
Figure 3A:
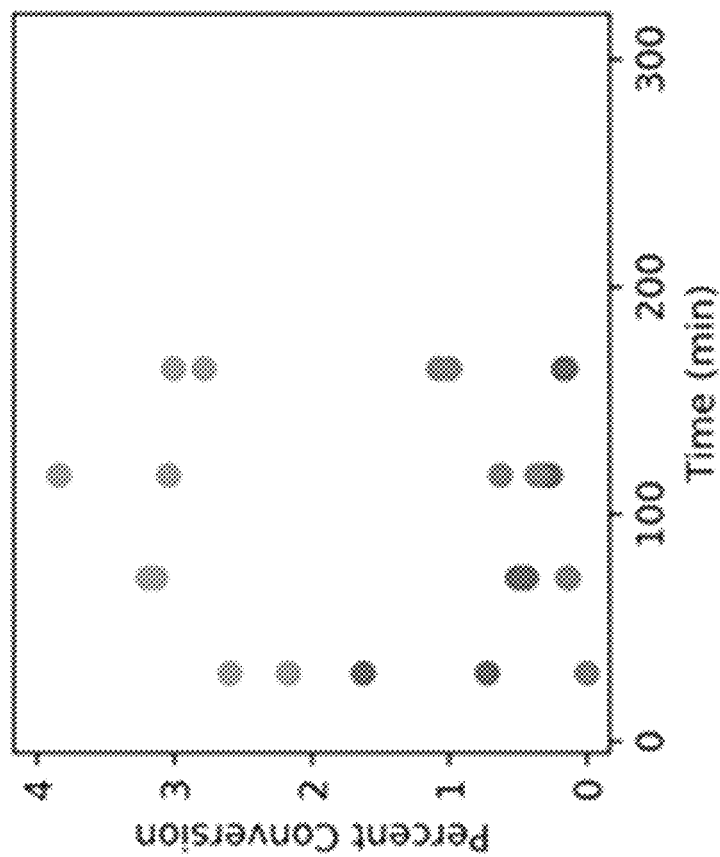
FIGS. 3A and 3B show percent conversion to benzyl alcohol, benzaldehyde, and benzoic acid as a function of time for experiments with 0.1 m or 0.4 m $CuCl_2$, respectively, and 0.12 molal toluene.
Figure 3B:
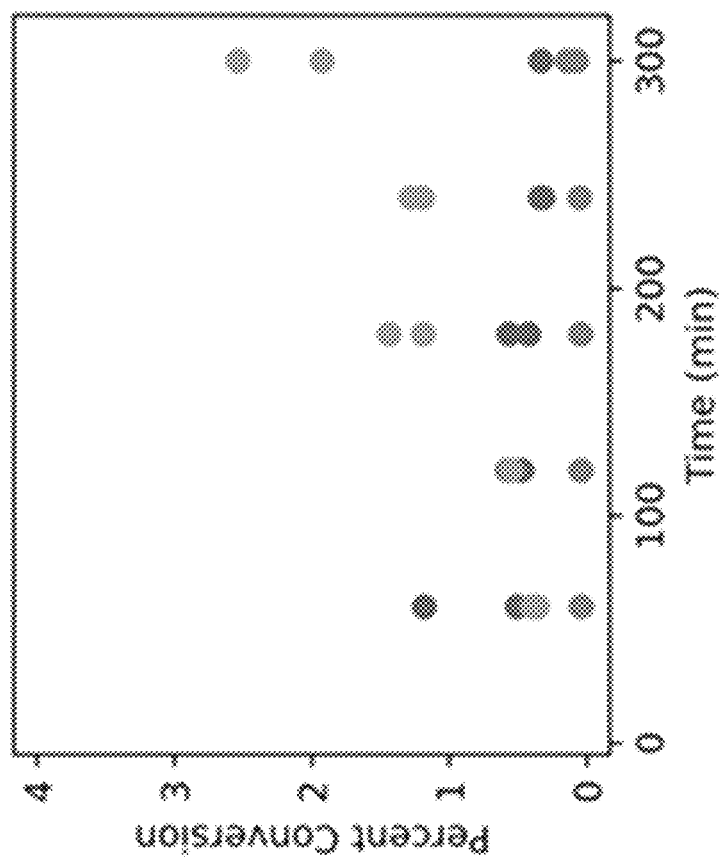

Time-series data are presented in Table 2 and the oxidation of benzene by $CuSO_4$ and by $CuCl_2$ are illustrated FIGS. 1 and 2, respectively. All experiments were conducted at 250° C. under anoxic conditions in fused silica tubes, using the general experimental procedures and analyses outlined previously. When $CuSO_4$ was used as the oxidant, conversion was ~40% after 121 hours with no other major products. When $CuCl_2$ was used as the oxidant, conversion was comparatively slower, only ~20% after 141 hours. The experiments involving copper sulfate were performed in duplicate to confirm the replicability of this experimental process. Two sets of close time points in the copper chloride experiments had similar conversion, confirming reasonable replicability.

$FeCl_3$ also oxidized benzene to chlorobenzene, Similar to the Cu (II) experiments. This oxidation was slower and only achieved 2% conversion after 9 days at 250° C.

tionation is due to stable complexes with Cu(II) and its surroundings, it follows that the even higher formation constant for the aqueous $CuSO_4$ complex at hydrothermal temperatures would lead to even more disproportionation than at room temperature. The metallic copper observed at the end of the experiments can be explained by the powerful sulfate complexation leading to Cu(I) disproportionation.

Oxidation of Toluene

The general toluene oxidation reaction scheme is consistent with the data shown in FIGS. 2A, 2B, 3A, and 3B. In both cases, benzyl alcohol concentration appears to reach a maximum early in the experiments and decrease as benzaldehyde and electrophilic aromatic substitution (EAS) products form. Benzoic acid is produced slowly and only appears as benzaldehyde has higher concentrations. As shown in FIGS. 2A and 2B, benzaldehyde concentration decreases as benzoic acid concentration increases. This is consistent with benzaldehyde being an intermediate in the production of benzoic acid.

Experimental hydrothermal reactions with toluene and $CuCl_2$ produced benzyl alcohol, benzaldehyde, and benzoic acid (FIGS. 2A and 2B and Table 3). Overall conversion is greater with higher concentrations of $CuCl_2$, however, the same products form at both concentrations. The results show

TABLE 2

Conversion and molar concentration of organic compounds from hydrothermal experiments. The first set of experiments used $CuSO_4$ as an oxidant. The second set of experiments used $CuCl_2$ as an oxidant.

| Time (hr) | Conversion (%) | Benzene (mm) | Phenol (mm) | Mass Balance (%) |
|---|---|---|---|---|
| 20.4 | 19.7 | 179 | 43.9 | 77 |
| 20.4 | 14.8 | 245 | 42.4 | 99 |
| 46.0 | 28.5 | 197 | 78.3 | 95 |
| 46.0 | 30.5 | 133 | 58.2 | 66 |
| 69.2 | 34.1 | 151 | 78.1 | 79 |
| 69.2 | 35.9 | 153 | 85.6 | 82 |
| 92.2 | 39.1 | 129 | 82.9 | 73 |
| 92.2 | 39.6 | 120 | 78.7 | 69 |
| 121.3 | 44.0 | 114 | 89.5 | 70 |
| 121.3 | 39.8 | 115 | 76.0 | 66 |

| Time (hr) | Conversion (%) | Benzene (mm) | Chlorobenzene (mm) | Mass Balance (%) |
|---|---|---|---|---|
| 0.5 | 0.2 | 188 | 0.3 | 65 |
| 23 | 10.6 | 200 | 23.6 | 77 |
| 24 | 9.8 | 250 | 27.2 | 96 |
| 45 | 14.7 | 203 | 35.0 | 82 |
| 48 | 15.0 | 228 | 40.2 | 92 |
| 72 | 18.2 | 209 | 46.4 | 88 |
| 144 | 20.7 | 228 | 59.5 | 99 |

To investigate the strengths of the aqueous $CuSO_4$ complexes, the thermodynamic properties of $CuSO_{4(aq)}$ were estimated to find the dominant form of Cu(II) over a range of $CuSO_4$ concentrations. The speciation of $CuSO_4$ goes against the traditional notion that salts generally dissociate in water. At the 1 molal concentration of $CuSO_4$ used in these experiments, the copper in solution is speciated almost entirely as the aqueous neutral species. Ionic species are prevalent only when $CuSO_4$ concentration is less than 0.001 molal at 25° C. and less than 0.1 millimolal concentrations at 250° C. The $CuSO_4$ complex appears to have an effect on the fate of the copper and the benzene. The presence of sulfate leads to phenol and metallic Cu while $CuCl_2$ leads to an entirely different set of products.

The thermodynamic properties of Cu(I)-sulfate species are uncharacterized at these conditions, but the rapid disproportionation of $Cu_2SO_4$ in water implies there are no stable complexes of Cu(I) and $SO_4^{-2}$. If rapid dispropordecreasing concentrations of benzyl alcohol over time, consistent with the changing acid to alcohol ratio shown in FIGS. 3A and 3B. This is consistent with a reaction scheme in which benzyl alcohol forms first and reacts to yield different organic products. Benzaldehyde concentration increases at longer time scales, signifying that it is the product of benzyl alcohol oxidation. Benzoic acid concentration increases over time at the same time that benzaldehyde concentration begins to level out. The stepwise oxidation from the most reduced compound (toluene) to the most oxidized compound (benzoic acid) is demonstrated by the increasing benzoic acid to benzyl alcohol ratio. The reaction of toluene and Cu(II) also leads to the production of multiring EAS products consistent with benzyl toluene isomers. The EAS products are also reactive and lead to higher molecular weight compounds, increasing complexity, and multiple side products. The experiments were kept to durations under 5 hours to avoid the production of high molecular weight compounds.

TABLE 3

Experimental data and products from experiments.

| Time (min) | Starting CuCl$_2$ (mm) | Toluene (mm) | Benzaldehyde (mm) | Benzyl Alcohol (mm) | Benzoic Acid (mm) | 2 Ring Products (mm) | Mass Balance (%) |
|---|---|---|---|---|---|---|---|
| 30 | 400 | 85.8 | 3.1 | 2.0 | bdl | 2.5 | 78 |
| 30 | 400 | 87.9 | 2.6 | 0.9 | bdl | 2.3 | 78 |
| 72 | 400 | 106.8 | 3.8 | 0.6 | 0.2 | 3.4 | 96 |
| 72 | 400 | 109.4 | 3.8 | 0.5 | 0.2 | 3.4 | 98 |
| 117 | 400 | 81.8 | 4.6 | 0.4 | 0.8 | 3.6 | 76 |
| 117 | 400 | 105.7 | 3.6 | 0.3 | 0.4 | 3.4 | 95 |
| 164 | 400 | 98.8 | 3.3 | 0.2 | 1.2 | 3.2 | 89 |
| 164 | 400 | 86.6 | 3.6 | 0.2 | 1.3 | 2.9 | 79 |
| 60 | 100 | 83.6 | 0.5 | 1.4 | bdl | 0.2 | 71 |
| 60 | 100 | 90.1 | 0.4 | 0.6 | bdl | 0.1 | 76 |
| 120 | 100 | 90.0 | 0.7 | 0.7 | 0.1 | 1.0 | 77 |
| 120 | 100 | 82.1 | 0.7 | 0.6 | 0.1 | 1.0 | 70 |
| 180 | 100 | 85.8 | 1.7 | 0.5 | 0.1 | 1.2 | 74 |
| 180 | 100 | 86.0 | 1.4 | 0.7 | 0.1 | 1.3 | 75 |
| 240 | 100 | 85.7 | 1.4 | 0.4 | 0.1 | 1.9 | 75 |
| 240 | 100 | 91.9 | 1.5 | 0.4 | 0.1 | 2.5 | 80 |
| 300 | 100 | 75.5 | 2.3 | 0.2 | 0.1 | 2.8 | 67 |
| 300 | 100 | 90.4 | 3.0 | 0.4 | 0.2 | 2.3 | 80 |

Aromatic Dehalogenation

Figure 4A:
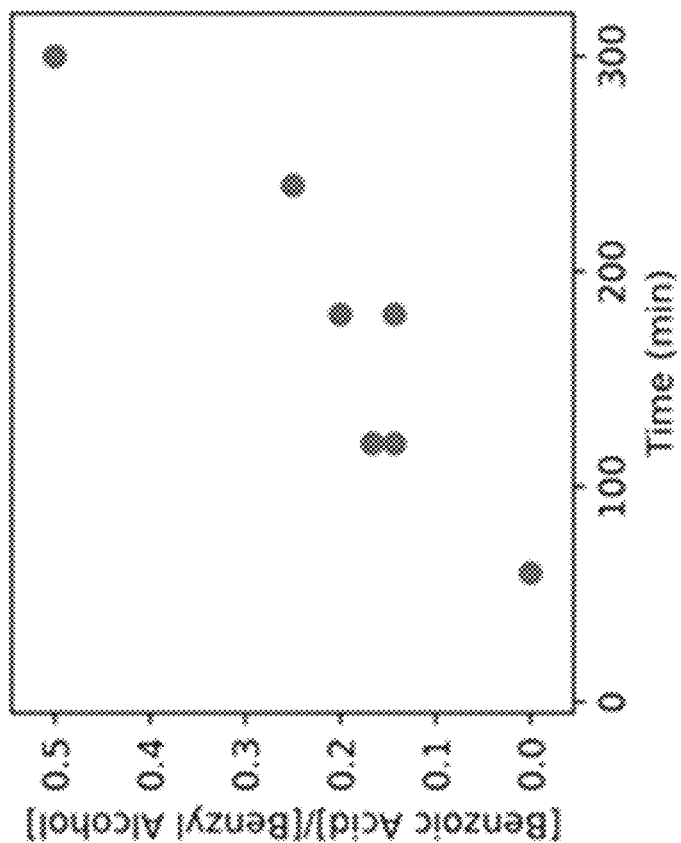
FIGS. 4A and 4B show acid to alcohol ratio over time for the data presented in FIGS. 3A and 3B, respectively.
Figure 4B:
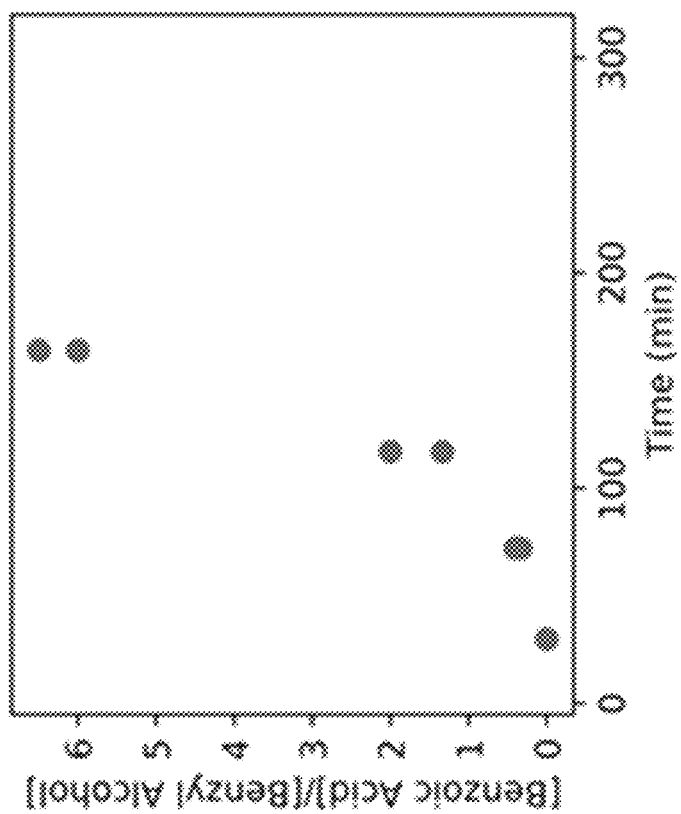
Figure 5A:
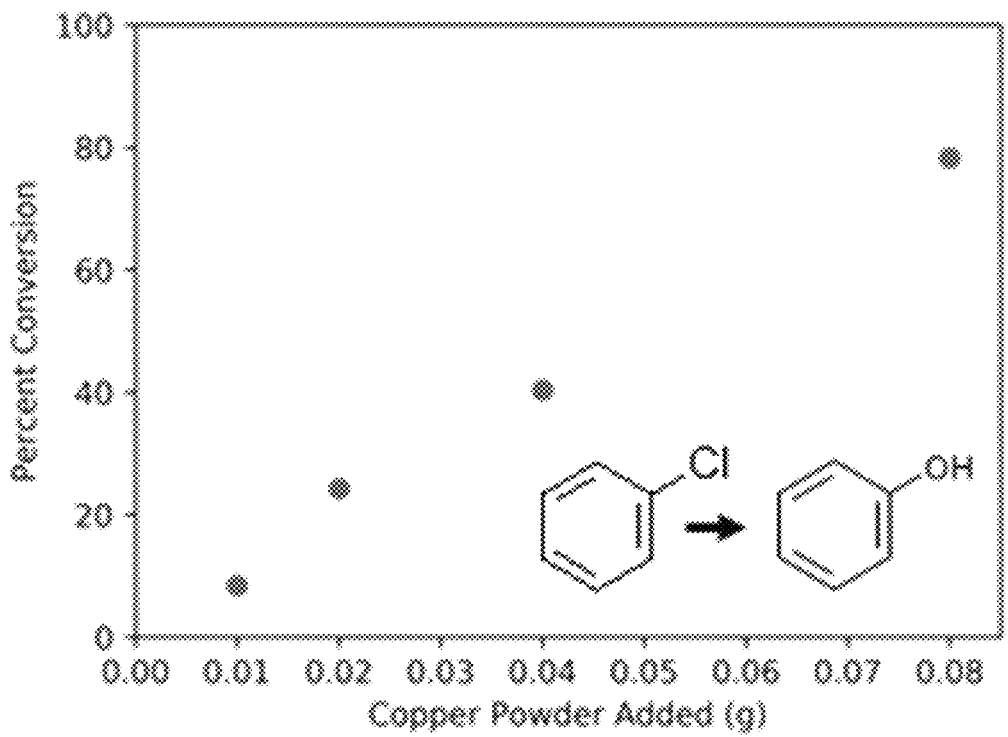
FIGS. 5A and 5B show percent conversion of chlorobenzene to phenol and benzene, respectively, over 47 hours under hydrothermal conditions using an initial volume of 8 chlorobenzene and the indicated amounts of copper powder.
Figure 5B:
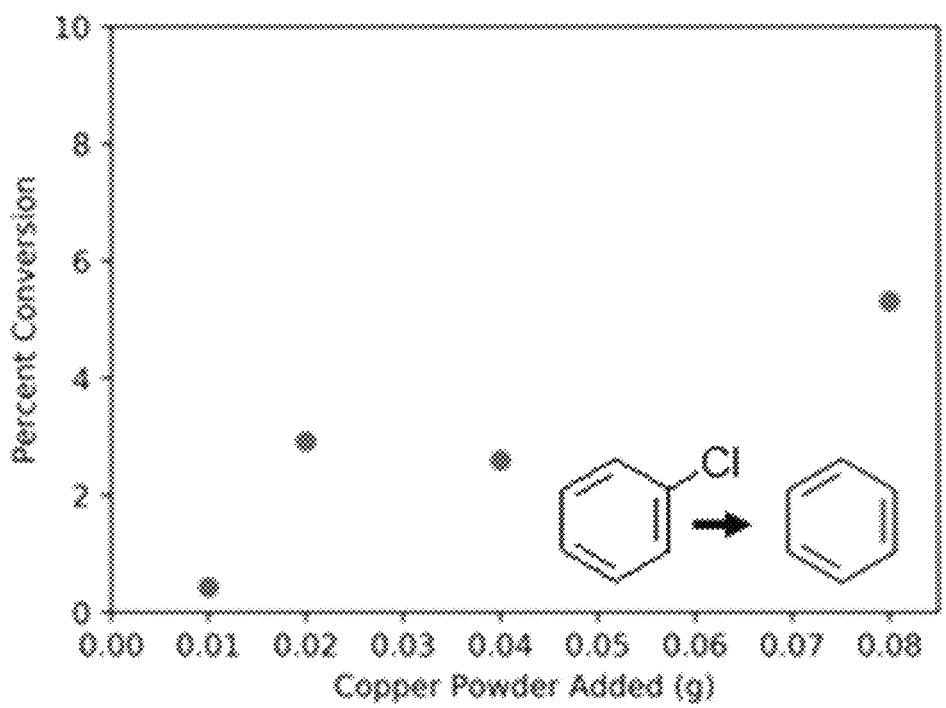
Figures 6A, 6B:
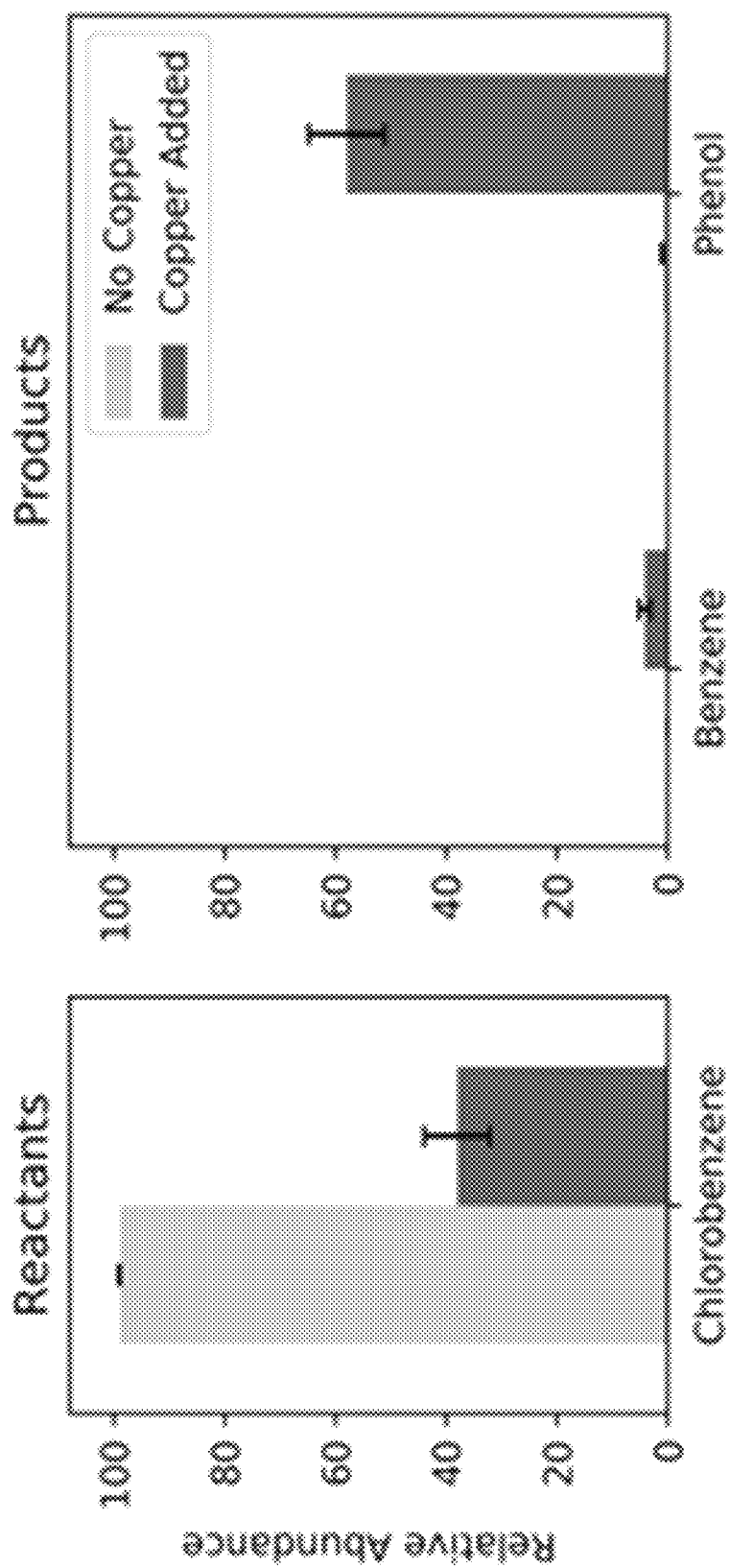
FIGS. 6A-6F show relative abundance of organic compounds after 42 hours at 250° C. with an initial chlorobenzene volume of 5 μL. Experiments were performed in duplicate, with and without 0.07 g copper. The values on the graph represent the mean of duplicates and the error bars are one standard deviation.
Figures 6C, 6D:
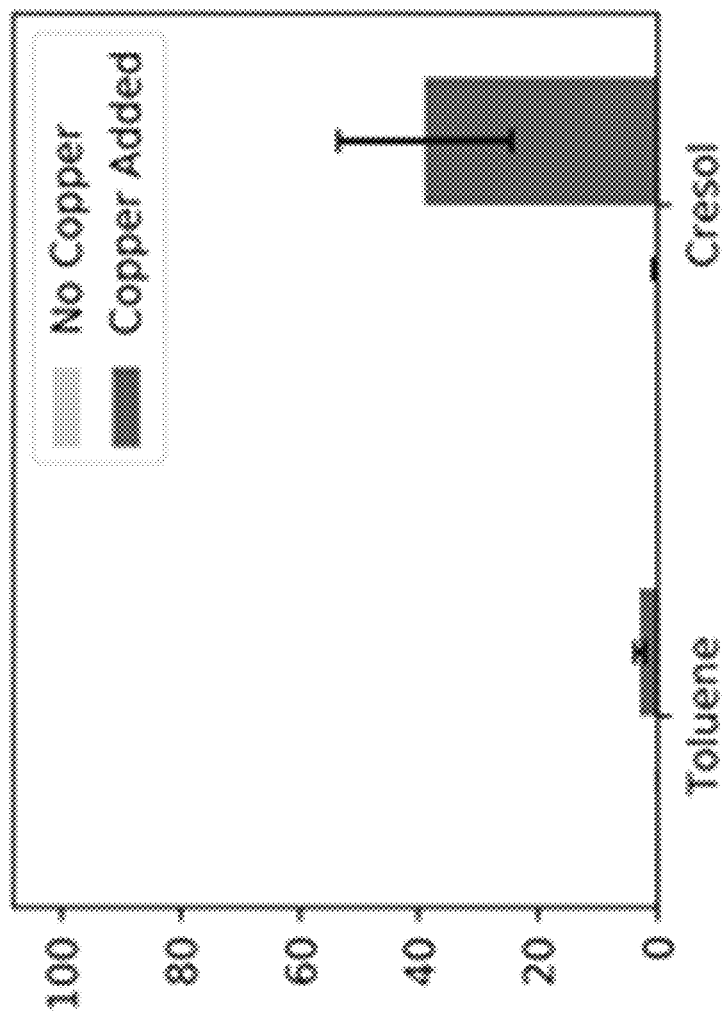
Figure 6F:
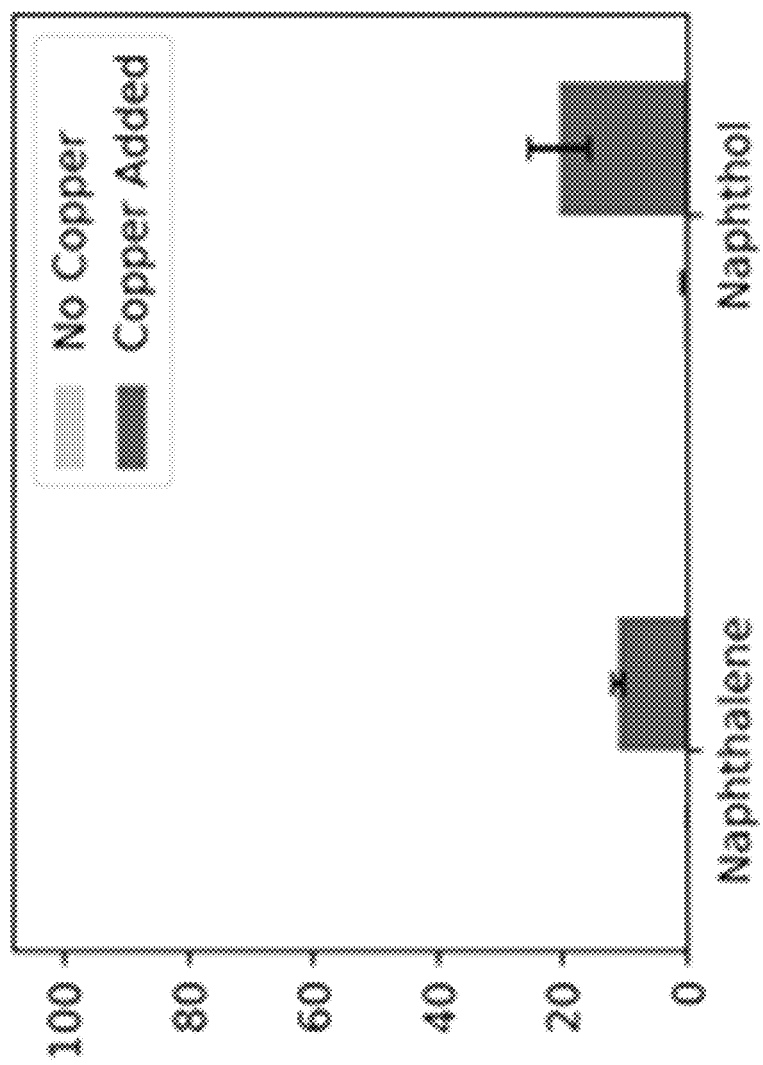
Figure 6E:
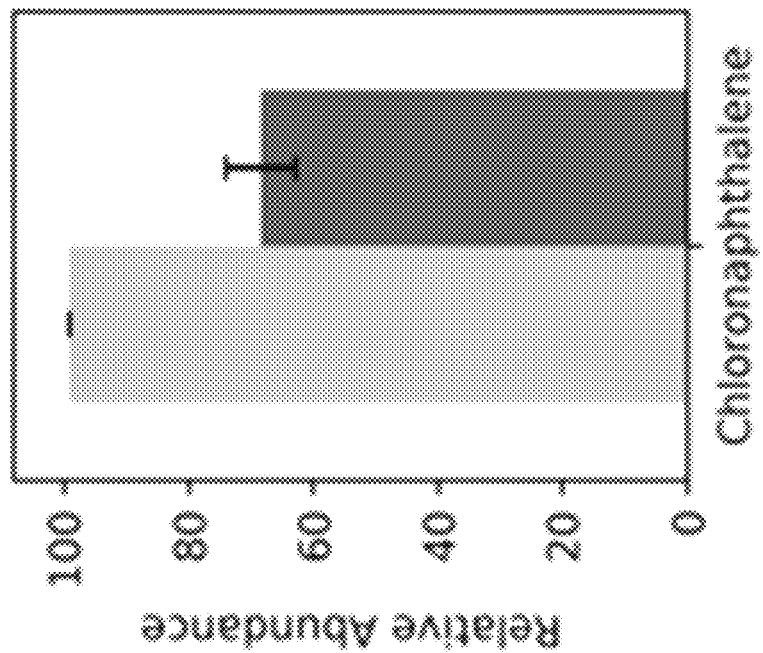

All experiments were conducted at 250° C. with >20 μm copper powder. In the first set of experiments, 8 μL of chlorobenzene, a concentration of 0.26 m, reacted with copper in 300 μL of water with variable amounts of copper to show the relationship between copper and overall conversion. In the second set of experiments, 5 μL of chlorobenzene, chlorotoluene, and chloronaphthalene were used with 300 μL water and 0.07 g of copper. The initial organic concentrations were 0.16 m, 0.14 m, and 0.12 m for chlorobenzene, chlorotoluene, and chloronaphthalene respectively. These compounds were chosen to see the effects of different functional groups while only using a single chloride group to limit the number of products. The amount of copper added to the experiments influences the conversion to phenol and benzene, as shown FIGS. 4A and 4B, which compare the amount of copper added and the percent of chlorobenzene converted over 47 hours. In these experiments, conversion is over 80% in experiments containing 0.08 g of copper powder, while experiments with 0.01 g of copper exhibit conversions of around 10%.

TABLE 4

Reaction parameters and results of hydrothermal experiments.

| Time (hr) | Cu Powder (g) | Initial Cl-Benzene (μL) | Cl-Benzene (mol %) | Benzene (mol %) | Phenol (mol %) | Mass Balance (%) |
|---|---|---|---|---|---|---|
| 42 | 0 | 5.0 | 99.1 | nd | 0.9 | 96 |
| 42 | 0 | 5.0 | 98.9 | nd | 1.1 | 99 |
| 42 | 0.07 | 5.0 | 42.1 | 4.9 | 53.0 | 77 |
| 42 | 0.07 | 5.0 | 33.7 | 3.4 | 62.9 | 85 |
| 47 | 0.08 | 8.0 | 16.4 | 5.3 | 78.3 | 76 |
| 47 | 0.04 | 8.0 | 57.1 | 2.6 | 40.3 | 96 |
| 47 | 0.02 | 8.0 | 72.8 | 2.9 | 24.3 | 92 |
| 47 | 0.01 | 8.0 | 91.1 | 0.4 | 8.4 | 97 |

| Time (hr) | Cu Powder (g) | Initial Cl-Toluene (μL) | Cl-Toluene (mol %) | Toluene (mol %) | Cresol (mol %) | Mass Balance (%) |
|---|---|---|---|---|---|---|
| 42 | 0 | 5.0 | 99.2 | nd | 0.8 | 97 |
| 42 | 0 | 5.0 | 99.2 | nd | 0.8 | 99 |
| 42 | 0.07 | 5.0 | 68.9 | 2.4 | 28.7 | 72 |
| 42 | 0.07 | 5.0 | 47.1 | 3.5 | 49.4 | 69 |

| Time (hr) | Cu Powder (g) | Initial Cl-Naphthalene (μL) | Cl-Naphthalene (mol %) | Naphthalene (mol %) | Naphthol (mol %) | Mass Balance (%) |
|---|---|---|---|---|---|---|
| 42 | 0 | 5.0 | 99.1 | nd | 0.9 | 98 |
| 42 | 0 | 5.0 | 99.1 | nd | 0.9 | 98 |
| 42 | 0.07 | 5.0 | 64.4 | 11.7 | 23.9 | 71 |
| 42 | 0.07 | 5.0 | 72.4 | 10.5 | 17.1 | 79 |

The results of a functional group comparison are shown in FIGS. 6A-6F, which show relative abundance of organic compounds after 42 hours at 250° C. with an initial chlorobenzene volume of 5 μL. Experiments were performed in duplicate, with and without 0.07 g copper. The values on the graphs represent the mean of duplicates and the error bars are one standard deviation. Multiple halogenated aromatic compounds were reacted in order to determine the influence of addition functional groups on the ring. In all cases, there was greater conversion to dehalogenated products when copper was added. When no copper was present, the reaction was slow, and more than 98% of the aryl halide remained in solution after the experiment. When copper was added to the solution there was more than 10× higher conversion to the dehalogenated products. The alcohol to hydrocarbon ratio is highest in the chlorobenzene experiments and lowest in the chloronaphthalene experiments.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of oxidizing a first aromatic compound in the presence of a metal salt to yield a second aromatic compound, the method comprising:
    combining the first aromatic compound, the metal salt, and water in a reaction vessel to yield an aqueous mixture;
    sealing the aqueous mixture in the reaction vessel; and
    heating the aqueous mixture under anoxic conditions in the reaction vessel at a temperature exceeding 200° C. for a length of time in a range from 25 hours to 125 hours to yield a reaction product comprising the second aromatic compound,
    wherein the first aromatic compound is benzene, the metal salt is copper sulfate, and the second aromatic compound is phenol.

2. The method of claim 1, wherein a selectivity of the reaction exceeds 96%.

3. The method of claim 1, wherein a yield of phenol exceeds 40%.

4. The method of claim 1, wherein the reaction product comprises copper metal.

5. The method of claim 1, wherein the heating occurs under hydrothermal conditions.

6. The method of claim 1, wherein the reaction vessel is a glass reaction vessel.

7. The method of claim 1, further comprising removing oxygen from the water before combining the first aromatic compound, the metal salt, and the water in the reaction vessel.

8. The method of claim 7, wherein removing oxygen from the water comprises sparging the water with argon.

9. The method of claim 1, further comprising removing oxygen from the reaction vessel after sealing the aqueous mixture in the reaction vessel.

10. The method of claim 9, wherein removing oxygen from the reaction vessel comprises removing air from the reaction vessel.

11. The method of claim 10, wherein removing air from the reaction vessel comprises evacuating the reaction vessel to a pressure of less than 80 mTorr.

* * * * *